United States Patent
Shnaper et al.

(10) Patent No.: US 9,642,564 B2
(45) Date of Patent: *May 9, 2017

(54) APPARATUS AND METHOD FOR EXTRA-CORPORAL CHEMICAL DETECTION AND MONITORING

(71) Applicant: TraceX Inc., Landenberg, PA (US)

(72) Inventors: Zinovy Shnaper, Monument, CO (US); Joseph Straub, Falls Church, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,364

(22) Filed: Sep. 17, 2015

(65) Prior Publication Data

US 2016/0000361 A1    Jan. 7, 2016

Related U.S. Application Data

(63) Continuation of application No. 14/024,232, filed on Sep. 11, 2013, now Pat. No. 9,241,661.

(51) Int. Cl.
*A61B 5/145*    (2006.01)
*A61B 5/00*    (2006.01)

(52) U.S. Cl.
CPC ........ *A61B 5/14542* (2013.01); *A61B 5/0022* (2013.01); *A61B 5/14532* (2013.01); *A61B 5/14546* (2013.01); *A61B 5/4845* (2013.01); *A61B 5/4866* (2013.01); *A61B 5/681* (2013.01); *A61B 5/6829* (2013.01); *A61B 5/6831* (2013.01); *A61B 5/7282* (2013.01); *A61B 2560/0214* (2013.01); *A61B 2560/0242* (2013.01); *A61B 2562/04* (2013.01)

(58) Field of Classification Search
CPC ... A61B 5/14542; A61B 5/4845; A61B 5/681; A61B 5/6829; A61B 5/6831
See application file for complete search history.

(56) References Cited

U.S. PATENT DOCUMENTS

| | | | |
|---|---|---|---|
| 8,657,744 B2 * | 2/2014 | Rompa | A61B 5/14542 600/309 |
| 2013/0006066 A1 * | 1/2013 | Melton | A61B 5/4845 600/309 |

* cited by examiner

*Primary Examiner* — Eric Winakur
(74) *Attorney, Agent, or Firm* — Miodrag Cekic; Intellectual Property Strategists, LLC

(57) ABSTRACT

A device for detection of substances transmitted into the body surrounding environment through body boundaries including a first sensor arranged to face a body boundary surface and structured to locally detect a substance indicative of at least one targeted substance of interest transmitted through the body boundary surface in proximity of the body boundary surface of a monitored subject. The device also includes a second sensor arranged to face in an opposite direction from the body boundary surface and structured to detect in a surrounding environment at least one substance indicative of the targeted substance of interest transmitted through the body boundary surface of the monitored subject. In addition the device further include an electronic circuit structured to receive and process the signals generated by the first and second sensors, and to determine presence of the at least one targeted substance of interest.

20 Claims, 3 Drawing Sheets

*Prior Art*

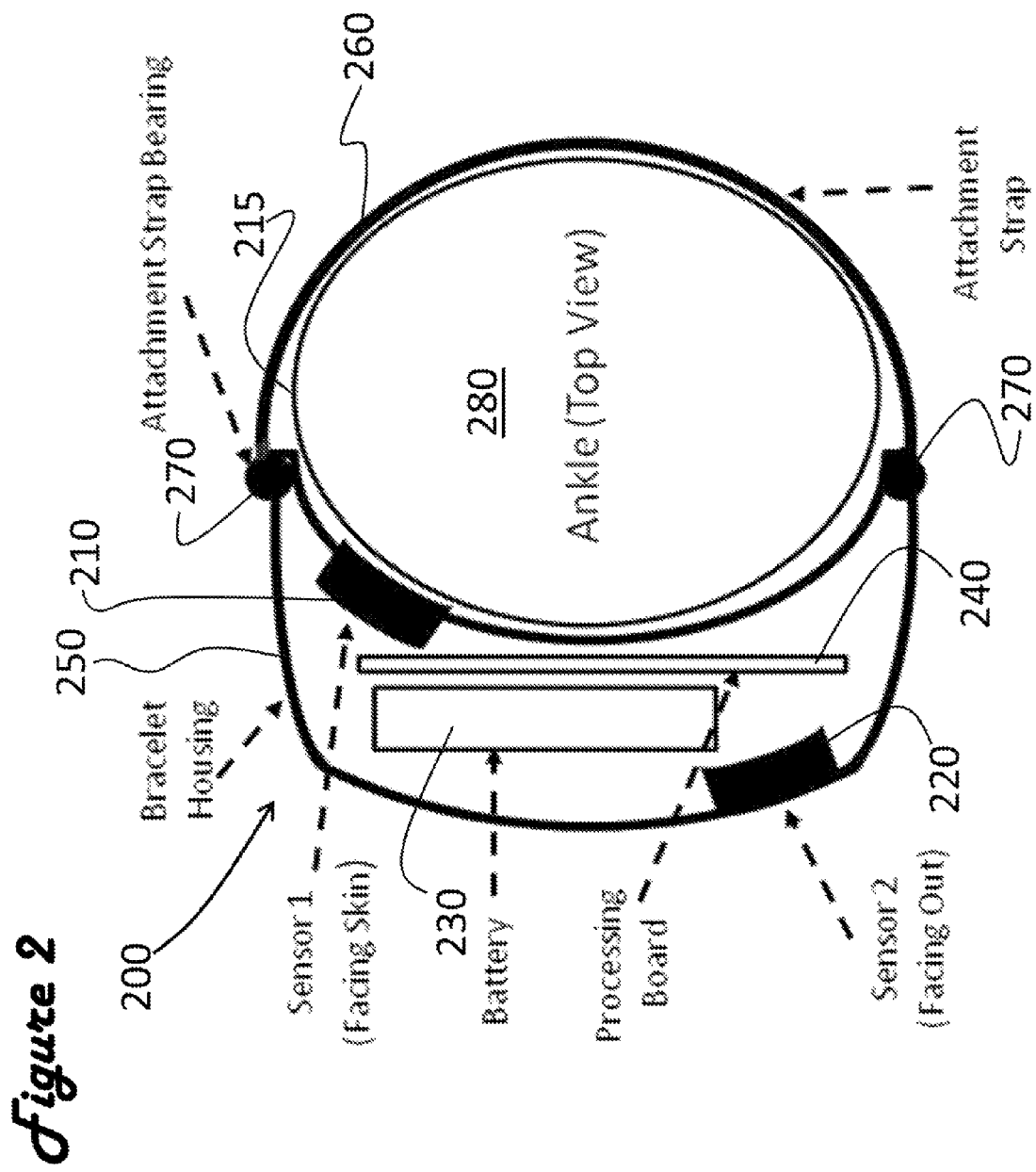

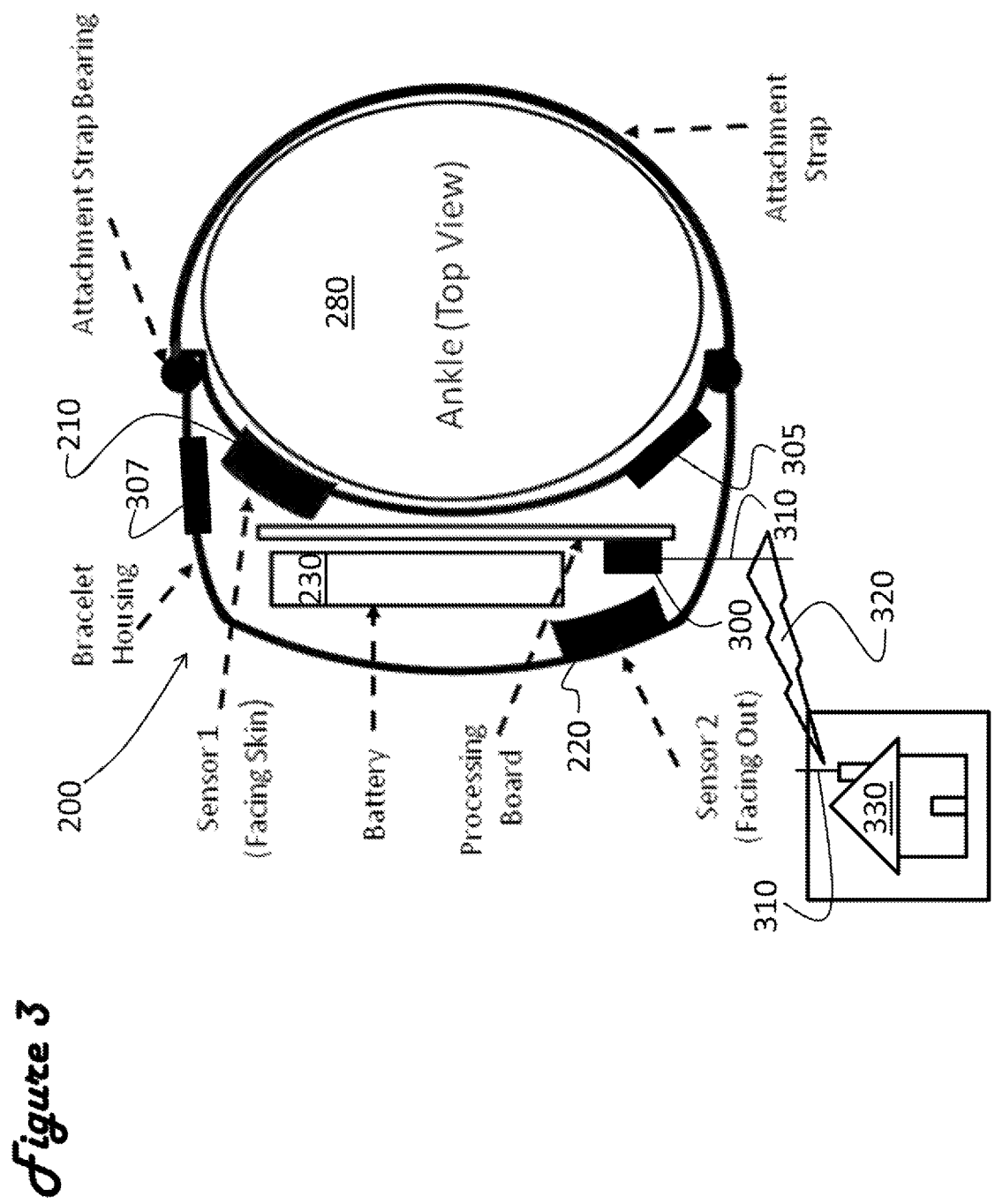

APPARATUS AND METHOD FOR EXTRA-CORPORAL CHEMICAL DETECTION AND MONITORING

RELATED APPLICATIONS

The current Application is a Continuation Application of U.S. application Ser. No. 14/024,232, filed Sep. 13, 2013, (which is incorporated by reference herein) of which the current Application claims priority and other benefits. Both, the current Continuation Application and the parent U.S. application Ser. No. 14/024,232 claim priority benefit of U.S. Provisional Application Ser. No. 61/701,764, filed Sep. 17, 2012, which is also incorporated by reference herein in its entirety.

FIELD OF THE INVENTION

The current invention relates to a method and an apparatus for chemical detection and monitoring of compounds pertinent to biological functions of an organism utilizing a sensing and monitoring devices arranged in proximity of the organism boundaries. More particularly, the current invention pertains to physic-chemical sensors and detectors arranged to be attached and to be worn in proximity to the organism's epidermis.

BACKGROUND OF THE INVENTION

Contemporary technology may provide solutions for several applications requiring frequent and timely detection and monitoring of conditions of a biological organism or a person using analysis of metabolic products transmitted into the surrounding environment through boundaries including epithelium, epidermis, and/or mucosal membranes. Of this, methods and apparata arranged to detect components of excretory fluids (e.g. liquids pertinent to perspiration or diaphoresis or vapors pertinent to transpiration embodiments directed toward monitoring of alcohols may be of particular interest because of its relative predominance in law enforcement practices. For example, transdermal alcohol monitoring using an ankle bracelet may be an accepted solution for repeat "Driving Under the Influence" (DUI) offenders. Such a device is known to be embraced by a plurality of jurisdictions in the US and UK. Current class of transdermal bracelets have been introduced in early 2000s, and since then there has been steadily increasing deployments each year.

The devices and methods in accordance to the current invention may be related to devices optimized for detection and testing of targeted substances transmitted through at least one body boundary surface including, but not limited to, epithelium, epidermis, skin, and/or mucosal membranes. One feature contrasting the devices of the current invention from known breathalyzers may be the extent of the duration of the measuring process. Namely, the breathalyzers may be optimized for relatively infrequent short measurements under controlled or commanded conditions, while the current invention may be arranged for prolonged or frequently repeated detection and measurement during an extensive duration of time under potentially constantly variable circumstances.

In some embodiments of the current invention, an active detecting element similar to an alcohol sensor commonly used in breathalyzers may be employed. For example, such a sensor, incorporated in a bracelet, may take regular frequent reading of the vapors transpired through the body boundary of the monitored subject of interest in order to detect the presence of alcohol in the subject's body, thereby determining events of alcohol consumption. One possible challenge, in existing alcohol monitoring bracelets of the prior art, may be events of detections of false positives and negatives. Substantially all of the existing sensors detect alcohol non-exclusively, and therefore detect other reacting substances present in the surrounding environment. In addition, a number of lotions and other skin products may contain alcohol. Therefore, significant sources potentially leading to false positives may include environmental factors and/or substances unrelated to consumption of alcoholic beverages applied intentionally or unintentionally in the proximity of the monitored subject epidermis. Thus, the prior art bracelets that may incorporate a position alcohol sensor that is placed in close proximity and faces the subject's body boundary surface may be inherently suboptimal regarding false positives. They may attempt to remedy the above feature by application of complex algorithms arranged to assist in determining alcohol consumption events by monitoring and complexly processing data received from the single sensor. The above algorithms may look at the time dependence and rate of rise and fall of the alcohol readings to attempt to differentiate true alcohol consumption events. In addition, in order to decrease the percentage of false positives, the bracelet detectors of the prior art may be tuned to a less sensitive setting, therefore missing a number of low level alcohol consumption events which may be of concern for law enforcement agencies.

The apparata and methods of the current inventions may be based on application of at least two separated sensors or sensor arrays disposed at certain distance from each other and arranged to sample body-related and environment related samples generally with adjustable sensitivity levels, efficacies, and/or sampling frequencies. The analysis of such enriched set of measurement results may result in more representative alcohol consumption detections less sensitive to the false positives and negatives.

It may be noted that the apparata and the methods of the present invention may not be limited to the application involving alcohols only. Different embodiments of the current invention may be utilized in cases where other constituents of perspired or transpired fluids may be of interest. For the applications pertinent to, but not limited by, detections of lactic acid and lactates, urea, Na, Cu, Fe, Cr, Ni, Pb, 2-methilphenol (o-cresol), 4-methylphenol (p-cresol), sugars, and combinations and mixtures of the above are not exceeding the scope of the current invention. Furthermore, the detection of perspired water may be accomplished using the current invention, for example in order to monitor diaphoresis and other conditions (e.g. hyperthyroidism, hypoglycemia, menopause, diabetic ketoacidosis, renal insufficiency, pheochromolytoma, etc.) related to frequent or abnormal perspiration.

It should be noted that in some embodiments "subjects of interest" may include animals capable of transpiration or transmission of substances through pertinent body boundaries. Such embodiments may be of interest in agriculture, recreation, sports, veterinarian medical practice, and/or in practices associated with usage of animals in health-related research and testing.

SUMMARY OF THE INVENTION

A device for detection of substances transmitted into the body surrounding environment through body boundaries including a first sensor arranged to face at least one body boundary surface and structured to locally detect a substance indicative of at least one targeted substance of interest transmitted through the at least one body boundary surface in a proximity of the at least one body boundary surface of at least one monitored subject. The device also includes a second sensor arranged to face in an opposite direction from the at least one body boundary surface and structured to detect in a surrounding environment at least one substance indicative of the at least one targeted substance of interest transmitted through the at least one body boundary surface of the at least one monitored subject. In addition the device further include an electronic circuit structured to receive and process the signals generated by the first and second sensors, and to determine presence of the at least one targeted substance of interest.

BRIEF DESCRIPTION OF THE DRAWINGS

FIG. 2 illustrates methods and devices in accordance with the current invention.
FIG. 3 illustrates methods and devices in accordance with the current invention.

DETAILED DESCRIPTION OF THE INVENTION

The current invention may be better understood by referring to the following descriptions, which should be read in conjunction with the accompanying drawings of particular exemplary embodiments. This description of the illustrated embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also understand that such equivalent assemblies do not depart from the spirit and scope of the invention in its broadest form.

Figure 1:
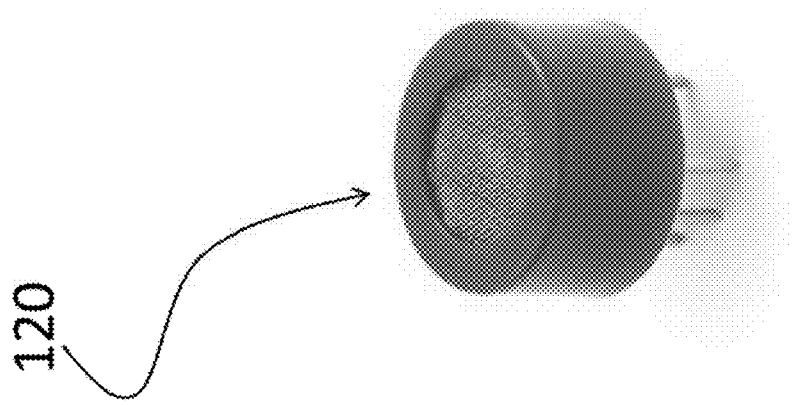
FIG. 1 illustrates prior art devices.
Figure 1:
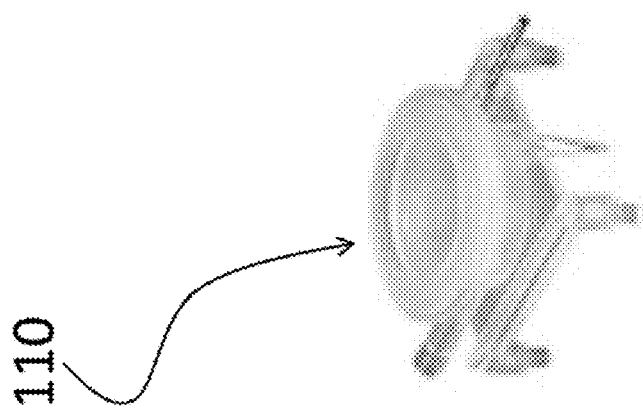
Figure 1:
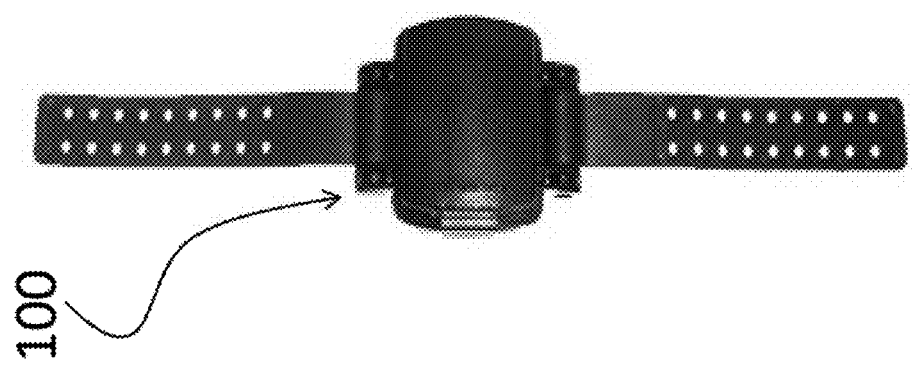

The FIG. 1 illustrates an alcohol monitoring bracelet 100 of prior art. One should note that different alcohol monitoring bracelets 100 may incorporate a single alcohol sensor represented by either a fuel cell alcohol sensor 110 or a semiconductor alcohol first sensor 120 (both well known to the practitioners and commercially available from a plurality of sources).

One embodiment of the methods and devices in accordance with the present invention is descriptively illustrated in FIG. 2. The monitoring device 200 incorporates at least one first sensor 210 arranged in a proximity of and to face toward, when in active usage, at least one body boundary surface 215, and at least one second sensor 220 arranged to face out in opposite direction from the at least one body boundary surface 215, i.e. toward the environment in the more distant vicinity of the at least one body boundary surface. The first sensors 210 may be structured to collect body-related samples and generate at least one signal indicative of presence of the at least one targeted substance resulting from the at least one substance transmitted through the at least one body boundary surface. The second sensors 220 may be structured to collect and sample collocated environment-related samples and generate at least one signal indicative of presence of at least one targeted substance corresponding to (e.g. substantially similar to, resulting from, or otherwise indicative of) the targeted substance transmitted through the at least one body boundary surface.

The monitoring device may be powered by at least one electric power source 230 (e.g. replaceable battery, battery rechargeable by in situ or at remote recharging stations, or permanently installed "extended life" sources), and include at least one electronic circuitry, for example incorporated into at least one processing board 240 structured to receive and process the signals generated by the sensors and determine, with desired sensitivity, presence of the at least one targeted substance of interest being originated in the body and transpired through the at least one body boundary surface under monitoring.

In the illustrated embodiment, the above structure may be enclosed in a housing 250 arranged to be attached to the attachment strap 260 (e.g. via at least one articulated attachment strap bearings 270). The monitoring device 200 may be attached to at least one body part (e.g. ankle 280) of the monitored subject, such that the at least one sensor 210 remains in proximity and facing the body boundary surface 215 (e.g. skin) of the monitored subject of interest, without undue discomfort or undue restriction of the monitored subject's abilities to function (e.g. to move at customary speed and perform common daily routines and/or obligations).

In some embodiments, by detecting, monitoring, and recording the presence of alcohol containing vapors in the environment using the at least one second sensor 220 and comparing the acquired data with the data obtained by the at least one firsts sensor 210 in the proximity of the at least one body boundary surface 215, a differential reading may be obtained. Such differential reading may be used to provide data more certain as to the source of the detection event. For example, if the subject enters an environment that has significant alcohol vapors, then a comparable reading on both the at least one first sensors 210 and the at least one second sensor 220 may confirm that situation and not report alcohol consumption by the monitored subject. As an alternative embodiment, as the monitored subject imbibes at a location where there are other alcohol vapors—as soon as the subject exits, the at least one outside facing second sensor 220 may no longer report, but the at least one body boundary surface facing first sensor 210 does report—thus confirming an alcohol consumption event. The at least two sensor technique may enable the monitoring device 200 to operate relatively more sensitively, having enhanced capabilities of detecting lower level drinking events and, at the same time, keep the percentage of false positives to an acceptable level. Both, the at least one first sensor 210 and the at least one second sensor 220 may be connected to an internal microcontroller, for example, integrated with at least one processing board 240, running algorithms comparing the data from the at least first sensors 210 and the at least second sensors 220, and making determinations on the probable nature of the events.

A different embodiment is illustrated in the schematic in FIG. 3. The device schematically illustrated in FIG. 3 may incorporate a plurality of body boundary facing first sensors 210, and/or a plurality of environment ("Out") facing second sensors 220 which may further enhance accuracy and reliability of alcohol consumption effects.

The at least one group (of at least two) of body boundary facing first sensors 210, and/or another group (of at least one) of environment ("Out") facing second sensors 220 may be utilized in a different set of embodiments. The groups of first and second sensors, may be arranged as at least one sensor array 305 (arrays may incorporate distinct sensing elements) structured (depending on the particular embodiments) to function in parallel (e.g. contributing to common first sensor and/or second sensor signals), or may be pared (e.g. pertinent portions of the first sensor array 305 with a corresponding portion of the second sensor arrays 307) to generate a differential signal.

In addition, such arrangements may be more efficient in application where detection and monitoring of alternative constituents of the perspired or transpired fluids (e.g. lactates, cresols, and or sugars) which may be present (in addition or in alternative) in diminutive quantities relative to aforementioned alcohols. For this class of embodiments, the aforementioned features of the current invention pertinent to operations with enhanced sensitivities may be of particular interest.

In addition, the monitoring device 200 may include at least one communication subsystem 300 structured to form and maintain communicative connections (e.g. including a digital signal transponder wedge with a transponder transistor amplifier to enhance the signal). The at least one communication subsystem 300 may use at least one conformal or no-conformal antenna 310 for communication of data (either raw detection signals or processed information) via at least one wired, wireless, or combined communication links 320 to at least one remote party of interest 330 communicatively connected to the at least one communication subsystem 300 via at least one communication link 320. The at least one remote party of interest 330 may include, but are not limited to, law enforcement agencies or detachments, medical personnel, emergency responders, supervisors and guardians, family members, designated contact persons, and similar.

While specific values, relationships, materials and components have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now set forth the embodiments and certain modifications of the concepts under the present invention, various other embodiments as well as certain variations and modifications of the embodiments herein shown and described will obviously occur to those skilled in the art upon becoming familiar with such underlying concepts. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

We claim:

1. A method for detection and classification of events relating to substances transmitted into the body surrounding environment through body boundaries comprising steps of:

providing at least one first sensor arranged proximally to face at least one body boundary surface and structured to collect a plurality of body-related samples and generate at least one signal indicative of presence of at least one targeted substance of interest in a proximity of the at least one body boundary surface of at least one monitored subject;

providing at least one second sensor arranged to face in an opposite direction from the at least one body boundary surface and structured to collect a plurality of environment-related samples and generate at least another signal indicative of presence of at least one targeted substance of interest or a substance substantially similar to or resulting from the at least one targeted substance of interest in a surrounding environment of the at least one monitored subject;

wherein the at least one one sensor and the at least one second sensor have adjustable sensitivity levels;

providing at least one electronic circuit communicatively connected to the at least one first sensor and the at least one second sensor and arranged to receive and process the at least one signal generated by the at least one first sensor and the at least one signal generated by the at least one second sensor, and to determine based on a differential reading when an event of presence of the at least one targeted substance of interest as being transpired through the at least one body boundary surface of the at least one monitored subject has occurred;

collecting at least one body-related sample and generating, using the at least one first sensor, at least one signal indicative of at least one targeted substance resulting from the at least one substance transmitted through the at least one body boundary surface of at least one monitored subject;

collecting in a surrounding environment at least one environment-related sample and generating, using the at least one second sensor, at least one signal indicative of at least one targeted substance corresponding to the targeted substance transmitted through the at least one body boundary surface of the at least one monitored subject;

determining, using least one electronic circuit, when an event of presence of the at least one targeted substance of interest as being transpired through the at least one body boundary surface has occurred based on a differential computed by subtraction of the at least one signal generated by the at least one second sensor from the at least one signal generated by the at least one first sensor.

2. The method of claim 1, wherein the at least one targeted substance of interest have been chosen from the set of substances consisting of alcohols, lactic acid and lactates, urea, Na, K, Ca, Mg, Zn, Cu, Fe, Cr, Ni, Pb, cresols, 2-methilphenol (o-cresol), 4-methylphenol (p-cresol), sugars, and combinations and mixtures of the above substances.

3. The method of claim 1, wherein the at least electronic circuitry incorporates at least one processing board locally connected to at least one an internal microcontroller, structured to make determinations on a probable nature of the detection of the at least one targeted substance and generate a signal indicative of consumption of the at least one targeted substance by the at least one monitored subject.

4. The method of claim 1, further including at least one electric power source.

5. The method of claim 4, wherein at least one electric power source have been chosen from the group of power sources consisting of a replaceable battery, an in situ rechargeable battery, a battery rechargeable by a remote recharging stations, a permanently installed extended life battery, and any combination of the above batteries.

6. The method of claim 4, wherein the at least one electronic circuit have been protectively surrounded by at least one housing attached to at least one attachment strap, and wherein the at least one housing and the at least one attachment strap have been arranged for connectivity via at least one articulated attachment strap bearing.

7. The method of claim 6, wherein the at least one housing have been arranged to be attached to at least one body part of the at least one monitored subject, such that the at least one first sensor remains in proximity and facing the body boundary surface of the monitored subject, without undue restriction of the monitored subject's abilities to function.

8. The method of claim 1, comprising additional step of providing at least one communication subsystem structured to be communicatively connected with to at least one remote party of interest via at least one communication link.

9. The method of claim 8, wherein the at least one remote party of interest has been chosen from the group consisting of law enforcement agencies and detachments, medical personnel, emergency responders, supervisors, guardians, family members, designated contact persons, and combination of the above.

10. The method of claim 8, wherein the at least one communication subsystem includes at least one antenna arranged for communicating information over at least one communication link chosen from the group consisting of wired communication links, wireless communication links, and combined communication links.

11. A method for detection and classification of events relating to substances transmitted into the body surrounding environment through body boundaries comprising steps of:
provliding at least one first sensor array arranged proximally to face at least one body boundary surface and structured to collect a plurality of body-related samples and generate at least one signal indicative of presence of at least one targeted substance of interest in a proximity of the at least one body boundary surface of at least one monitored subject;
providing at least one second sensor array arranged to face in an opposite direction from the at least one body boundary surface and structured to collect a plurality of environment-related samples and generate at least another signal indicative of presence of at least one targeted substance of interest or a substance substantially similar to or resulting from the at least one targeted substance of interest in a surrounding environment of the at least one monitored subject;
wherein the at least one first sensor array the at least one second sensor array have adjustable sensitivity levels;
providing at least one electronic circuit communicatively connected to the at least one first sensor array and the at least one second sensor array and arranged to receive and process the at least one signal generated by the at least one first sensor array and the at least one signal generated by the at least one second sensor array, and to determine based on a differential reading when an event of presence of the at least one targeted substance of interest as being transpired through the at least one body boundary surface of the at least one monitored subject has occurred;
collecting at least one body-related sample and generating, using the at least one first sensor array, at least one signal indicative of at least one targeted substance resulting from the at least one substance transmitted through the at least one body boundary surface of at least one monitored subject;
collecting in a surrounding environment at least one environment-related sample and generating, using the at least one second sensor array, at least one signal indicative of at least one targeted substance corresponding to the targeted substance transmitted through the at least one body boundary surface of the at least one monitored subject;
determining, using least one electronic circuit, when an event of presence of the at least one targeted substance of interest as being transpired through the at least one body boundary surface has occurred based on a differential computed by subtraction of the at least one signal generated by the at least one second sensor array from the at least one signal generated by the at least one first sensor array.

12. The method of claim 11, wherein the at least one targeted substance of interest has been chosen from the set of substances consisting of alcohols, lactic acid and lactates, urea, Na, K, Ca, Mg, Zn, Cu, Fe, Cr, Ni, Pb, cresols, 2-methilphenol (o-cresol), 4-methylphenol (p-cresol), sugars, and combinations and mixtures of the above substances.

13. The method of claim 11, wherein the at least electronic circuitry incorporates at least one processing board locally connected to at least one an internal microcontroller, structured to make determinations on a probable nature of the detection of the at least one targeted substance and generate a signal indicative of consumption of the at least one targeted substance by the at least one monitored subject.

14. The method of claim 11, further including at least one electric power source.

15. The method of claim 14, wherein at least one electric power source have been chosen from the group of power sources consisting of a replaceable battery, an in situ rechargeable battery, a battery rechargeable by a remote recharging stations, a permanently installed extended life battery, and any combination of the above batteries.

16. The method of claim 11, wherein the at least one electronic circuit have been protectively surrounded by at least one housing attached to at least one attachment strap, and wherein the at least one housing and the at least one attachment strap have been arranged for connectivity via at least one articulated attachment strap bearing.

17. The method of claim 16, wherein the at least one housing have been arranged to be attached to at least one body part of the at least one monitored subject, such that the at least one first sensor remains in proximity and facing the body boundary surface of the monitored subject, without undue restriction of the monitored subject's abilities to function.

18. The method of claim 11, comprising additional step of providing at least one communication subsystem structured to be communicatively connected with to at least one remote party of interest via at least one communication link.

19. The method of claim 18, wherein the at least one remote party of interest has been chosen from the group consisting of law enforcement agencies and detachments, medical personnel, emergency responders, supervisors, guardians, family members, designated contact persons, and combination of the above.

20. The method of claim 18, wherein the at least one communication subsystem includes at least one antenna arranged for communicating information over at least one communication link chosen from the group consisting of wired communication links, wireless communication links, and combined communication links.

* * * * *